United States Patent [19]

Schoen et al.

[11] Patent Number: 5,532,251
[45] Date of Patent: Jul. 2, 1996

[54] METHOD OF TREATING CARDIAC ARRHYTHMIA WITH 3-BENZOYL-3, 7-DIAZABICYCLO[3.3.1]NONANE COMPOUNDS

[75] Inventors: Uwe Schoen, Burgdorf; Reinhard Brueckner; Joerg Meil, both of Hanover; Dirk Thormaehlen, Rheden, all of Germany

[73] Assignee: Kali-Chemie Pharma GmbH, Hanover, Germany

[21] Appl. No.: 382,265

[22] Filed: Feb. 1, 1995

[30] Foreign Application Priority Data

Feb. 1, 1994 [DE] Germany .......................... 44 02 933.0

[51] Int. Cl.⁶ .................................................. A61K 31/44
[52] U.S. Cl. .................................. 514/300; 514/821
[58] Field of Search ...................... 514/300, 821

[56] References Cited

U.S. PATENT DOCUMENTS

| | | | |
|---|---|---|---|
| 4,459,301 | 7/1984 | Binnig et al. | 424/267 |
| 4,550,112 | 10/1985 | Schoen et al. | 514/278 |
| 4,556,662 | 12/1985 | Binnig et al. | 514/300 |
| 4,742,172 | 5/1988 | Schoen et al. | 546/122 |
| 4,912,113 | 3/1990 | Schoen et al. | 514/278 |
| 4,959,373 | 7/1990 | Lubisch et al. | 514/300 |
| 5,164,401 | 11/1992 | Burow et al. | 514/300 |

FOREIGN PATENT DOCUMENTS 2658558  6/1978  Germany .

OTHER PUBLICATIONS

CA 111:115218, Lubisch et al., 1989.

*Primary Examiner*—Kimberly Jordan
*Attorney, Agent, or Firm*—Evenson, McKeown, Edwards & Lenahan

[57] ABSTRACT

The use of 3-benzoyl-3,7-diazabicyclo[3.3.1]nonane compounds of the general formula I

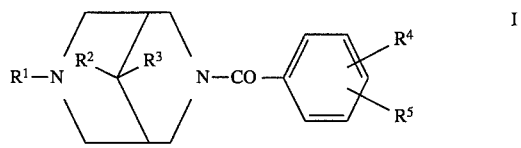

in which
  $R^1$ is an alkyl group having 1–6 carbon atoms or a cycloalkylalkyl group having 4–7 carbon atoms,
  $R^2$ and $R^3$ are each individually lower alkyl or together form an alkylene chain having 3–6 carbon atoms,
  $R^4$ is hydrogen, halogen, cyano, nitro, trifluoromethyl or a $R^6$—$SO_2$— group, in which $R^6$ is fluorine or lower alkyl, and
  $R^5$ is hydrogen, halogen, trifluoromethyl or nitro, or their physiologically acceptable acid addition salts for the treatment of cardiac arrhythmias in larger mammals, including humans.

2 Claims, No Drawings

METHOD OF TREATING CARDIAC ARRHYTHMIA WITH 3-BENZOYL-3,7-DIAZABICYCLO[3.3.1]NONANE COMPOUNDS

BACKGROUND OF THE INVENTION

The present invention relates to the use of 3,7,9,9-tetrasubstituted 3,7-diazabicyclo[3.3.1]nonane compounds which carry in the 3-position an optionally substituted benzoyl radical for the treatment of cardiac arrhythmias and to the production of medicaments suitable for this treatment.

Hoerlein et al., Published German Patent Application No. DE-OS 2,658,558 discloses 3-alkanoyl- and 3-aroyl-3,7-diazabicyclo[3.3.1]nonane derivatives which are only described as having central analgesic activity.

SUMMARY OF THE INVENTION

It is the object of this invention to provide a novel method of treating cardiac arrhythmia in large mammals.

Another object of the invention is to provide antiarrhythmically active pharmaceutical preparations having an improved activity profile.

These and other objects are achieved in accordance with the invention by providing a method of treating cardiac arrhythmia in a larger mammal comprising administering to the mammal an effective cardiac rhythm affecting amount of a 3-benzoyl-3,7-diazabicyclo[3.3.1]nonane compound corresponding to formula I

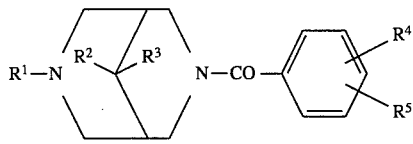

wherein
- $R^1$ is an alkyl group having 1–6 carbon atoms or a cycloalkylalkyl group having 4–7 carbon atoms,
- $R^2$ and $R^3$ are each individually lower alkyl or together form an alkylene chain having 3–6 carbon atoms,
- $R^4$ is hydrogen, halogen, cyano, nitro, trifluoromethyl or a $R^6$—$SO_2$— group in which $R^6$ is fluorine or lower alkyl, and
- $R^5$ is hydrogen, halogen, trifluoromethyl or nitro, or a physiologically acceptable acid addition salt thereof.

DETAILED DESCRIPTION OF PREFERRED EMBODIMENTS

It has now been found that a group of 3-benzoyl-3,7-diazabicyclo[3.3.1]nonane compounds falling within the scope of Published German Patent Application No. DE-OS 2,658,558 exhibit an antiarrhythmic activity profile which makes them suitable for the treatment of cardiac arrhythmias, in particular tachycardic arrhythmias.

According to the invention, the agents used for the production of antiarrhythmically active pharmaceutical preparations for the treatment of cardiac arrhythmias in larger mammals, including humans, are 3-benzoyl-3,7-diazabicyclo-[3.3.1]nonane compounds of the general formula I

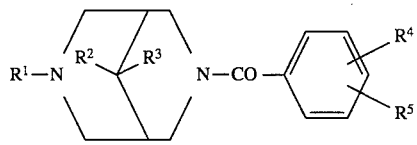

in which
- $R^1$ is an alkyl group having 1–6 carbon atoms or a cycloalkylalkyl group having 4–7 carbon atoms,
- $R^2$ is lower alkyl and
- $R^3$ is lower alkyl or
- $R^2$ and $R^3$ together form an alkylene chain having 3–6 carbon atoms,
- $R^4$ is hydrogen, halogen, cyano, nitro, trifluoromethyl or the $R^6$—$SO_2$— group, in which $R^6$ is fluorine or lower alkyl, and
- $R^5$ is hydrogen, halogen, trifluoromethyl or nitro, and
their physiologically acceptable acid addition salts.

If $R^1$ in the compound of formula I is an alkyl group, this can be straight-chain or branched and contain 1–6, preferably 3–5, carbon atoms. A cycloalkylalkyl group $R^1$ can contain 4–9, preferably 4–7, carbon atoms. Alkyl radicals having 3–5 carbon atoms have proven to be particularly suitable $R^1$ radicals.

If the substituents $R^2$ and $R^3$ are lower alkyl, these alkyl groups can be the same or different and may be straight-chain or branched and contain 1–4, preferably 1–3, carbon atoms and be, in particular, methyl. If $R^2$ and $R^3$ together form an alkylene group, this can contain 3–6, preferably 4–5, carbon atoms. Compounds in which $R^2$ and $R^3$ together are an alkylene chain having 4–5 carbon atoms have proven particularly suitable. The substituent $R^4$ of the benzoyl radical is preferably halogen. If $R^4$ is an $R^6$—$SO_2$— group, a lower alkyl group $R^6$ contained therein can contain 1–4 carbon atoms and be, in particular, methyl.

Suitable physiologically acceptable acid addition salts of the compounds of the formula I include salts with inorganic acids, e.g. hydrohalic acids, in particular hydrochloric acid, or sulfuric acid, or with organic acids, for example lower aliphatic monocarboxylic or dicarboxylic acids such as acetic acid, malonic acid, fumaric acid, tartaric acid, lactic acid, maleic acid, or citric acid, or aromatic carboxylic acids such as e.g. salicylic acid, or even organic sulfonic acids, for example lower alkylsulfonic acids such as methanesulfonic acid or benzenesulfonic acids optionally substituted in the benzene ring by halogen or lower alkyl, such as p-toluenesulfonic acid.

The compounds of formula I employed according to the invention for treating cardiac arrhythmias fall within the scope of the 3-aroyl-3,7-diazabicyclo[3.3.1]nonane compounds having central analgesic effects described in Published German Patent Application No. DE-OS 2,658,558 and in some cases are disclosed in this published application.

It has now surprisingly been found that when the group of compounds of formula I and their physiologically acceptable acid addition salts are used according to the invention, they have antiarrhythmic effects. In particular, they exhibit class III antiarrhythmic properties and cause a prolongation of the effective refractory period in the heart, which leads to a prolongation of the QT interval in the ECG. The compounds have a favorable activity profile with good tolerability, a long duration of action and such a high selectivity of the antiarrhythmic action to bradycardic and hypotensive properties that in the antiarrhythmically active dose range a therapeutically undesired effect on the heart rate and/or the blood pressure does not occur. The compounds are distinguished in that the antiarrhythmic activity is particularly highly pronounced under tachycardic conditions.

The antiarrhythmic activity of the compounds can be confirmed by standard pharmacological test methods.

Description of the pharmacological test methods

1. Determination of the minimum toxic dose.

Male mice weighing 20 to 25 g were administered maximum doses of 300 mg/kg of the test substance p.o. The animals were observed carefully for toxicity symptoms for 3 hours. All symptoms and instances of death over a period of 72 hours after administration were additionally recorded. Concomitant symptoms were likewise observed and recorded. If death or severe toxic symptoms was observed, increasingly lower doses were administered to other mice until toxic symptoms no longer occurred. The lowest dose which caused death or severe toxic symptoms is indicated in the following Table A as the minimum toxic dose. The Example numbers listed in Table A refer to the subsequent Preparation Examples.

TABLE A

| Test substance Example No. | Minimum toxic dose mg/kg mouse p.o. |
|---|---|
| 4 | >300 |
| 6 | >300 |
| 8 | >300 |
| 15 | >300 |
| 17 | >300 |
| 18 | >300 |
| 20 | >300 |

2. In vivo investigation of the antiarrhythmic properties of the substances under tachycardic conditions in anaesthetized guinea-pigs.

The effects of the substances on the effective refractory period (=ERP) and the blood pressure on i.v. administration with increased heart rate were investigated on anaesthetized guinea-pigs. A bipolar stimulation catheter was inserted into the right ventricle of the animals via a jugular vein under full anesthesia. The heart rate of the animals was maintained at about 150% of their normal heart rate via this by means of electrical stimulation during the entire investigation. A cannula for i.v. administration of the test substances was inserted in the other jugular vein. During the investigation, the systolic and the diastolic arterial blood pressure (=SAP and DAP) were measured in a carotid artery via a pressure gauge (Statham pressure transducer). The test substances were administered i.v. in increasing doses (cumulatively). Before administration of the first dose and in each case 8 minutes after administration of each dose, the ERP was determined by means of a double pulse protocol. The dose at which a prolongation of the ERP to 115% of the starting value was achieved was considered as the effective dose (=ERP-$ED_{115}$). Effective doses for a hypotensive effect were considered as the dose at which the SAP was decreased to 85% of its starting value (=SAP-$ED_{85}$), and the dose at which the DAP was decreased to 85% of its starting value (=DAP-$ED_{85}$).

The results obtained using the method described above are given in the following Table B. The Example numbers listed for the test substances refer to the subsequent Preparation Examples.

TABLE B

| Example No. | Antiarrhythmic activity ERP-$ED_{115}$ in µmole/kg i.v. | Blood pressure decrease $ED_{85}$ in µmole/kg i.v. | |
|---|---|---|---|
| | | DAP | SAP |
| 4 | 2 | >32 | >32 |
| 7 | 3.2 | 4 | 5 |

The activity of the substances in prolonging the refractory period can also be confirmed in in vitro tests by determination of the functional refractory period on the isolated papillary muscle of the right heart chamber of guinea-pigs.

The foregoing test results show that the compounds of the formula I have antiarrhythmic effects and clearly prolong the effective refractory period of the heart muscle and that an effective hypotensive action of the substances first occurs at doses which are significantly higher than the doses effective for prolongation of the refractory period.

Due to their activity profile described above, the substances are suitable for the suppression of tachycardic cardiac arrhythmias (extrasystoles, ventricular flutters and fibrillations) and can be used for the prophylaxis and treatment of cardiac arrhythmias in larger mammals, including humans. In particular, the substances are suitable for preventing the occurrence of tachyarrhythmias, i.e. arrhythmias which are coupled to an increase in the heart rate.

The doses to be used can be different from individual to individual and naturally vary depending on the type of condition to be treated, the substance used and the administration form. For example, parenteral formulations will in general contain less active compound than oral preparations. In general, however, pharmaceutical forms containing 0.5 to 100 mg, in particular 1 to 25 mg, of active agent per individual dose are suitable for administration to larger mammals, including humans.

The compounds can be contained, according to the invention, together with conventional pharmaceutical carriers, adjuvants and/or excipients in solid or liquid pharmaceutical preparations. Examples of solid preparations which may be mentioned include suppositories and orally administrable preparations such as tablets, coated tablets, capsules, powders or granules. These preparations can contain conventional pharmaceutical inorganic and/or organic excipients, such as e.g. talc, lactose or starch in addition to conventional pharmaceutical auxiliaries, for example lubricants or tablet disintegrating agents. Liquid preparations such as solutions, suspensions or emulsions of the active compounds can contain conventional diluents such as water, oils and/or suspending agents such as polyethylene glycols or the like. Other adjuvants can additionally be added, such as e.g. preservatives, flavoring agents and the like.

The active compounds can be mixed and formulated with the pharmaceutical adjuvants and/or excipients in a known manner. For example, in order to prepare solid pharmaceutical forms, the active compounds can be mixed with the auxiliaries and/or excipients in a customary manner and granulated by wet or dry processes. The granules or powder can be filled directly into capsules or compressed to give table cores in a customary manner. If desired, these can be sugar-coated in a known manner.

The compounds of the formula I can be prepared in a known manner by the processes described in the aforementioned Published German Patent Application No. DE-OS 2,658,558 or analogously to these processes. For example, compounds of formula I can be obtained by a process in which a compound corresponding to the general formula II

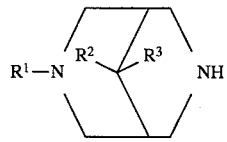

in which $R^1$, $R^2$ and $R^3$ have the above meanings, is acylated with an acid or a reactive acid derivative of the general formula III

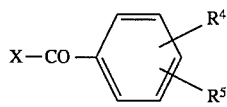

in which $R^4$ and $R^5$ have the above meanings, and X is hydroxyl or a reactive group, and if desired free compounds of formula I are converted to their physiologically acceptable acid addition salts, or the acid addition salts are converted to free compounds of formula I.

The reaction of the amines of formula II with the acids or acid derivatives of the formula III can be carried out by conventional methods for amide formation. Particularly suitable reactive acid derivatives of formula III include acid halides, preferably chlorides, and acid anhydrides. The acylation can be carried out in a solvent which is inert under the reaction conditions, if desired in the presence of an acid-binding agent. Suitable solvents include, for example, halogenated hydrocarbons such as dichloromethane, aromatic hydrocarbons such as benzene, cyclic ethers such as tetrahydrofuran or dioxane, dimethylformamide or mixtures of these solvents. Suitable acid-binding agents include inorganic bases, in particular alkali metal hydroxides, or organic bases such as tertiary lower alkylamines and pyridines.

The 3,7-diazabicyclo[3.3.1]nonane compounds of formula II used as starting materials are disclosed in Published German Patent Application No. DE-OS 2,658,558 and in Schoen et al., U.S. Pat. No. 4,406,640 and/or can be prepared in a known manner by the methods described in these specifications or analogously to the methods described in these specifications.

The following Examples are intended to illustrate the invention in further detail without restricting its scope in any way.

The following Examples 1 to 3 describe pharmaceutical preparations according to the invention containing an agent of the formula I and the production of such pharmaceutical preparations.

EXAMPLE 1: TABLETS

Composition (parts by weight):

| | |
|---|---|
| 3-(4-Chlorobenzoyl)-7-(n-butyl)-9,9-tetramethylene-3,7-diazabicyclo[3.3.1]nonane monohydrochloride | 20 parts |
| Maize starch | 30 parts |
| Lactose | 55 parts |
| Polyvinylpyrrolidone | 5 parts |
| Magnesium stearate | 2 parts |
| Talc | 3 parts |
| Total | 115 parts |

Preparation procedure:

The active compound was mixed with the maize starch and finely powdered lactose in a mixer. The resulting mixture was thoroughly moistened with a 20% strength solution of polyvinylpyrrolidone (Kollidon 25™ from BASF) in demineralized water. If necessary, more demineralized water is added. The moist granules were passed through a 2 mm sieve, dried at 40° C. on drying racks and then passed through a 1 mm sieve (Frewitt machine). After mixing the granules with magnesium stearate and talc, tablets with a weight of 115 mg each were compressed from the resulting mixture, such that each tablet contained 20 mg of active compound.

EXAMPLE 2: CAPSULES

Composition (parts by weight):

| | |
|---|---|
| 3-(2,4-Dichlorobenzoyl)-7-methyl-9,9-pentamethylene-3,7-diazabicyclo[3.3.1]nonane monohydrochloride | 20 parts |
| Maize starch | 20 parts |
| Lactose | 45 parts |
| Polyvinylpyrrolidone | 3 parts |
| Magnesium stearate | 1.5 parts |
| Highly disperse silica | 0.5 parts |
| Total | 90 parts |

Preparation procedure:

The active compound was mixed with the maize starch and finely powdered lactose in a mixer. The resulting mixture was thoroughly moistened with a 20% strength solution of polyvinylpyrrolidone (Kollidon 25™ from BASF) in demineralized water. If necessary, demineralized water is added. The moist granules were passed through a 1.6 mm sieve (Frewitt machine), dried at 40° C. on drying racks and then passed through a 1 mm sieve (Frewitt). After mixing the granules with magnesium stearate and highly disperse silica (Aerosil 200™ from Degussa), 90 mg portions of the resulting mixture were filled into size 4 hard gelatin capsules by means of an automatic capsule filling machine such that each capsule contained 20 mg of the active compound.

EXAMPLE 3: AMPOULES

Composition (per ampoule):

| | |
|---|---|
| 3-(2,4-Dichlorobenzoyl)-7-(n-butyl)-9,9-tetramethylene-3,7-diazabicyclo[3.3.1]nonane hydrochloride | 5 mg |
| Sodium chloride | 16 mg |
| Water for injection purposes | ad 2.0 mg |

Preparation procedure:

The sodium chloride was dissolved in water for injection purposes, and the active compound was added and dissolved with stirring. The solution was made up to the final volume using sufficient water for injection purposes. The batch was then passed through a 0.25µ membrane filter. Brown glass ampoules were each filled with 2.15 ml of solution and sealed. The ampoules were sterilized at 121° C. for 30 min using steam. 2 ml of injection solution contain 5 mg of active compound.

The following examples are intended to illustrate the preparation of the compounds of the formula I in greater detail.

EXAMPLE 4:
3-(4-Chlorobenzoyl)-7-(n-butyl)-9,9-tetramethylene-3,7-diazabicyclo[3.3.1]nonane.

4.38 g of 4-chlorobenzoyl chloride were added dropwise with stirring while cooling in ice to a solution of 5.91 g of 7-(n-butyl)-9,9-tetramethylene-3,7-diazabicyclo[3.3.1]nonane in a mixture of 80 ml of dichloromethane and 10 ml of aqueous sodium hydroxide solution. The reaction mixture was allowed to react for one hour. 100 ml of water were added, the organic phase was separated, and the aqueous phase was extracted twice with dichloromethane. The combined organic phases were dried with magnesium sulfate and concentrated. 8.6 g of 3-(4-chlorobenzoyl)-7-(n-butyl)-9,9-tetramethylene-3,7-diazabicyclo[3.3.1]-nonane were obtained as an oil which crystallized in the refrigerator. Melting point 105° to 107° C.

By reaction with isopropanolic hydrochloric acid solution, the title compound was converted to the corresponding hydrochloride having a melting point of 220° to 230° C.

EXAMPLES 5–30

The compounds of formula I listed in the following table were also obtained by the method described in Example 4. The following abbreviations are used in the table.
n=normal
i=iso
Cyp=cyclopropyl
HTa=hydrogen tartrate
HCl=hydrochloride may occur to persons skilled in the art, the invention should be construed broadly to include everything within the scope of the appended claims and equivalents thereof.

| Example No. | $R^1$ | $R^2$ | $R^3$ | $R^4$ | $R^5$ | Salt | Melting Point (°C.) |
|---|---|---|---|---|---|---|---|
| 5  | n-$C_4H_9$—   | $CH_3$— | $CH_3$— | H          | H         | 1 HCl    | 180–185   |
| 6  | n-$C_4H_9$—   | $CH_3$— | $CH_3$— | 4-$NO_2$   | H         | 1.5 HTa  | 97        |
| 7  | n-$C_4H_9$—   | $CH_3$— | $CH_3$— | 4-Cl       | H         | 1 HCl    | 196–198   |
| 8  | n-$C_4H_9$—   | $CH_3$— | $CH_3$— | 4-Br       | H         | base     | 99–101    |
| 9  | n-$C_4H_9$—   | $CH_3$— | $CH_3$— | 4-F        | H         | base     | 63–66     |
| 10 | n-$C_4H_9$—   | $CH_3$— | $CH_3$— | 4-CN       | H         | 1 HCl    | 246–250   |
| 11 | n-$C_4H_9$—   | $CH_3$— | $CH_3$— | 4-$SO_2CH_3$ | H       | 1.1 HCl  | 132–137   |
| 12 | n-$C_6H_{13}$—| $CH_3$— | $CH_3$— | 4-CN       | H         | 1.4 HTa  | amorphous |
| 13 | n-$C_6H_{13}$—| $CH_3$— | $CH_3$— | 4-$SO_2CH_3$ | H       | 1.4 HTa  | amorphous |
| 14 | n-$C_4H_9$—   | —$(CH_2)_4$— | | 4-CN   | H         | 1.4 HTa  | amorphous |
| 15 | n-$C_4H_9$—   | —$(CH_2)_4$— | | 4-Br   | H         | base     | 106–108   |
| 16 | n-$C_4H_9$—   | —$(CH_2)_4$— | | 4-F    | H         | base     | 85        |
| 17 | n-$C_4H_9$—   | —$(CH_2)_4$— | | 2-F    | 4-F       | 1 HCl    | 234       |
| 18 | n-$C_4H_9$—   | —$(CH_2)_4$— | | 2-Cl   | 4-Cl      | 1.1 HCl  | 237–239   |
| 19 | n-$C_4H_9$—   | —$(CH_2)_4$— | | 4-$NO_2$ | H       | 1 HCl    | 236–239   |
| 20 | n-$C_4H_9$—   | —$(CH_2)_4$— | | 4-$SO_2F$ | H      | 1 HCl    | 220       |
| 21 | n-$C_4H_9$—   | —$(CH_2)_4$— | | 4-$CF_3$ | H       | 1.4 HTa  | amorphous |
| 22 | n-$C_4H_9$—   | —$(CH_2)_4$— | | 4-$SO_2CH_3$ | H   | 1.4 HTa  | amorphous |
| 23 | n-$C_6H_{13}$—| —$(CH_2)_4$— | | 3-$NO_2$ | 5-$NO_2$| base     | 69.5      |
| 24 | i-$C_4H_9$—   | —$(CH_2)_5$— | | 4-Cl   | H         | 1 HCl    | 260–264   |
| 25 | Cyp-$CH_2$—   | $CH_3$— | $CH_3$— | 4-Cl       | H         | 1 HCl    | amorphous |
| 26 | n-$C_6H_{13}$—| $CH_3$— | $CH_3$— | 4-Cl       | H         | base     | 230–240   |
| 27 | $CH_3$—       | —$(CH_2)_5$— | | 2-Cl   | 4-Cl      | 1 HCl    | 255–257   |
| 28 | n-$C_4H_9$—   | —$(CH_2)_4$— | | 2-$NO_2$ | 4-Cl    | 1 HCl    | 156       |
| 29 | n-$C_3H_7$—   | n-$C_4H_9$— | $CH_3$— | 3-Cl     | H         | 1 HCl    | 236–238   |
| 30 | $C_2H_5$—     | —$(CH_2)_4$— | | 2-$CF_3$ | 5-$CF_3$| base     | 99–101    |

The foregoing description and examples have been set forth merely to illustrate the invention and are not intended to be limiting. Since modifications of the described embodiments incorporating the spirit and substance of the invention

What is claimed is:

1. A method of treating cardiac arrhythmia in a mammal comprising administering to said mammal an effective cardiac rhythm affecting amount of a 3-benzoyl-3,7-diazabicyclo[3.3.1]nonane compound corresponding to formula I

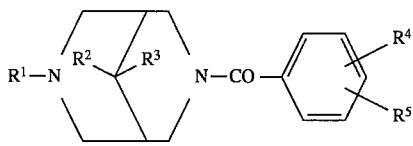

wherein

R¹ is an alkyl group having 1–6 carbon atoms or a cycloalkylalkyl group having 4–7 carbon atoms, R² and R³ are each individually lower alkyl or together form an alkylene chain having 3–6 carbon atoms, R⁴ is hydrogen, halogen, cyano, nitro, trifluoromethyl or a R⁶—SO₂— group in which R⁶ is fluorine or lower alkyl, and R⁵ is hydrogen, halogen, trifluoromethyl or nitro, or a physiologically acceptable acid addition salt thereof.

2. A method according to claim 1, wherein R¹ is an alkyl group having 3–5 carbon atoms; R² and R³ together are an alkylene chain having 4–5 carbon atoms; R⁴ is halogen, and R⁵ is hydrogen or halogen.

* * * * *